United States Patent [19]
Conway et al.

[11] Patent Number: 4,877,031
[45] Date of Patent: Oct. 31, 1989

[54] STEERABLE PERFUSION DILATATION CATHETER

[75] Inventors: Jean M. Conway, Mountain View; Peter R. McInnes, Sunnyvale, both of Calif.

[73] Assignee: Advanced Cardiovascular Systems, Inc., Mountain View, Calif.

[21] Appl. No.: 223,088

[22] Filed: Jul. 22, 1988

[51] Int. Cl.$^4$ .............................................. A61M 25/00
[52] U.S. Cl. ....................................... 128/344; 604/96
[58] Field of Search ................ 128/207.15, 344, 348.1; 604/96–103

[56] References Cited
U.S. PATENT DOCUMENTS

| | | | |
|---|---|---|---|
| 3,769,981 | 11/1973 | McWhorter | 604/96 |
| 4,198,981 | 4/1980 | Sinnreich | 128/344 |
| 4,289,128 | 9/1981 | Rusch | 128/207.15 |
| 4,423,725 | 1/1984 | Baran et al. | 128/207 |
| 4,581,017 | 4/1986 | Sahota | 604/101 |
| 4,641,654 | 2/1987 | Samson et al. | 128/344 |
| 4,661,094 | 4/1987 | Simpson | 604/53 |
| 4,762,129 | 8/1988 | Bonzel | 128/344 |
| 4,790,315 | 12/1988 | Mueller et al. | 128/344 |

FOREIGN PATENT DOCUMENTS
WO88/00071 1/1988 World Int. Prop. O. .......... 128/344

*Primary Examiner*—Dalton L. Truluck
*Attorney, Agent, or Firm*—Fulwider, Patton, Lee & Utecht

[57] ABSTRACT

A balloon dilatation catheter for PCTA and other vascular procedures which provides for the perfusion of blood when the balloon is inflated to dilate the artery or otherwise impede blood flow. The catheter comprises an elongated tubular member having an inner lumen extending along the length thereof, a perfusion body secured to the distal end of the tubular member having a small diameter lumen in fluid communication with the inner lumen of the tubular member, and a large diameter lumen which allows for the perfusion of blood through the perfusion body, and a balloon disposed about the perfusion body and secured around the periphery thereof in at least two circular locations. An inflation/-deflation port connects the small diameter lumen in the perfusion body to the interior of the balloon to pass inflation fluid therebetween. A guidewire is disposed within the small diameter inner lumen of the tubular member and facilitates the advancement of the catheter across the stenosis. When the balloon is inflated, blood proximal to the balloon passes through the large diameter lumen and discharges distally thereto.

10 Claims, 1 Drawing Sheet

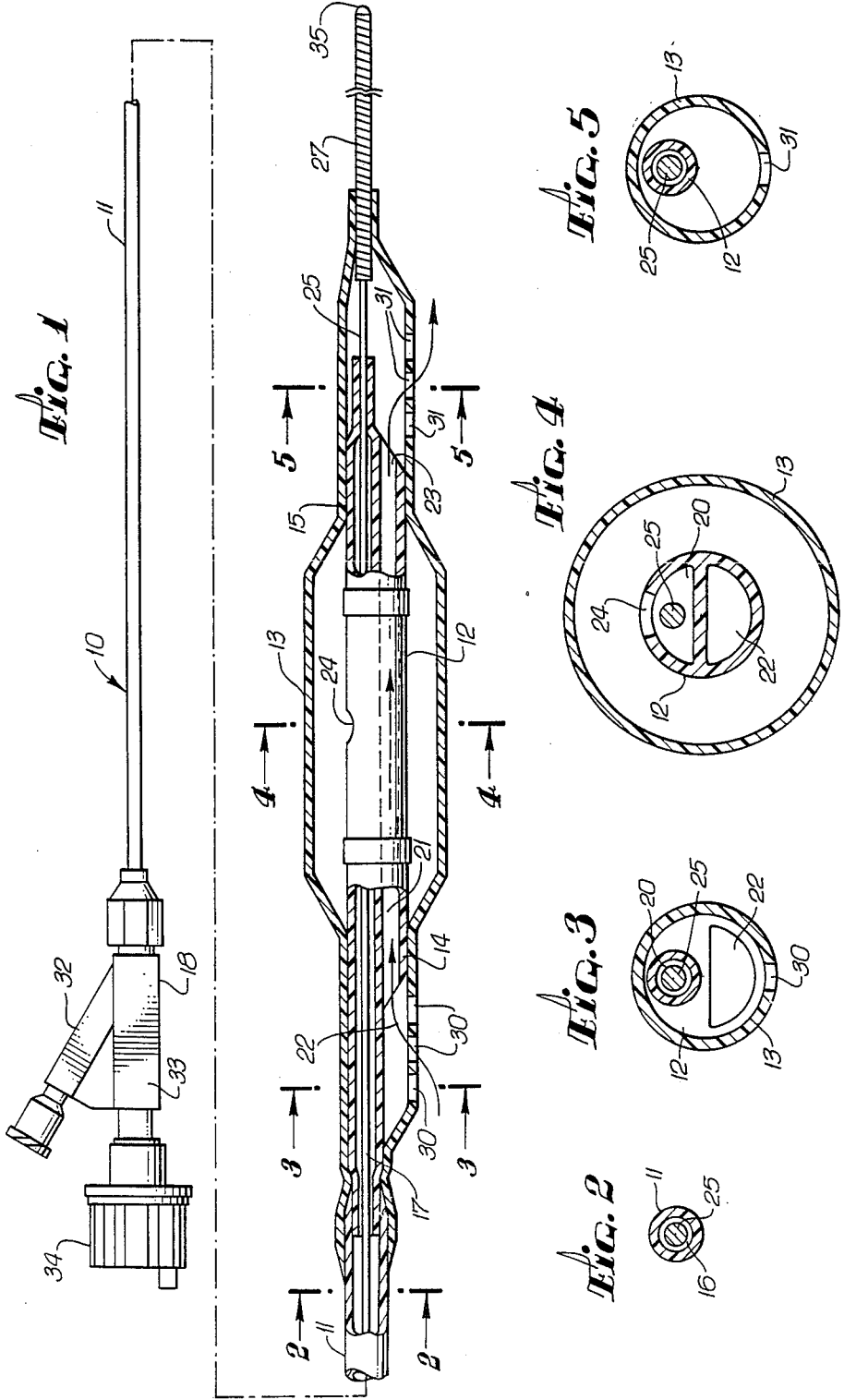

STEERABLE PERFUSION DILATATION CATHETER

BACKGROUND OF THE INVENTION

This invention generally relates to a dilatation catheter suitable for percutaneous transluminal angioplasty procedures which can perfuse blood distally of the dilatation balloon during the inflation thereof.

In typical percutaneous transluminal coronary angioplasty (PTCA) procedures, a guiding catheter having a preformed distal tip is percutaneously introduced into the cardiovascular system of a patient through tee brachial or femoral arteries and advanced therein until the distal tip thereof is in the ostium of the desired coronary artery. A guidewire and a dilatation catheter having a balloon on the distal end thereof are introduced through the guiding catheter with the guidewire slidably disposed within an inner lumen of the dilatation catheter. The guidewire is first advanced into the patient's coronary vasculature until the distal end thereof crosses the lesion to be dilated and then the dilatation catheter is advanced over the previously introduced guidewire until the dilatation balloon is properly positioned across the lesion. Once in position across the lesion, the flexible, relatively inelastic balloon is inflated to predetermined size with radiopaque liquid at relatively high pressures (e.g., greater than 8 atmospheres) to radially compress the atherosclerotic plaque of the lesion against the inside of the artery wall to thereby dilate the lumen of the artery. The balloon is then deflated so that the dilatation catheter can be removed and blood flow resumed through the dilated artery.

Further details of angioplasty procedures and the devices used in such procedures can be found in U.S. Pat. Nos. 4,332,254 (Lundquist); 4,323,071 (Simpson-Robert); 4,439,185 Lundquist); 4,468,224 (Enzmann et al.) 4,516,972 (Samson); 4,538,622 (Samson et al.); 4,554,929 (Samson et al.); and 4,616,652 (Simpson) which are hereby incorporated herein in their entirety.

Steerable dilatation catheters with built-in or fixed guidewires or guiding elements are used with greater frequency because the deflated profile of such catheters is generally smaller than conventional dilatation catheters with movable guidewires or elements having the same inflated balloon size. Further details of low-profile steerable, dilatation catheters may be found in U.S. Pat. Nos. 4,582,181 (Samson), 4,619,263 (Frisbie et al.), 4,641,654 (Samson et al.), and 4,664,113 (Frisbie et al.) which are hereby incorporated in its entirety by reference thereto. The lower profile of these catheters allows them to cross tighter lesions and to be advanced much deeper into the patient's coronary anatomy. Moreover, the use of steerable low-profile dilatation catheters shortens considerably the time for the angioplasty procedure because there is no need to first advance a guidewire across a lesion and then slide a conventional dilatation catheter over the previously advanced guidewire to position the balloon thereof across the lesion.

When the balloon is inflated during typical angioplasty procedures, all blood flow through the artery is blocked. While it is widely believed that long term dilation of the stenosis will increase the probability that the stenosis will remain open after dilation and will also reduce the risk of re-stenosis, presently used typical dilation times range from about 15 to 60 seconds because longer periods would result in dangerous ischemic conditions distally of the inflated balloon in a coronary region which may already be in jeopardy.

Efforts have been made to develop dilatation catheters which perfuse blood through the catheter or by the balloon of the catheter when the balloon is inflated during angioplasty procedure in order to avoid ischemic conditions distally of the balloon. For example the dilatation catheters described in U.S. Pat. Nos. 4,581,017 (Sahota) and 4,423,725 (Baran et al.) both describe means to perfuse blood distally when the dilatation balloon is inflated to facilitate longer inflation periods, but unfortunately both dilatation catheters are very complicated structurally and are expensive to manufacture. Additionally, any guidewire utilized with these catheters was disposed in the same lumen through which the blood must flow, thereby reducing the flow, unless the guidewire is withdrawn prior to the dilations to a location proximal to the perfusion inlet holes in the catheter body.

What has been needed and heretofore unavailable is a steerable dilatation catheter which provides for the distal perfusion of blood during angioplasty procedures through a lumen separate from the lumen receiving the guidewire to thereby allow for longer term dilations. The present invention satisfies that need.

SUMMARY OF THE INVENTION

This invention is directed to a steerable dilatation catheter which provides for the distal perfusion of blood through an inner lumen which passes through the balloon thereof when the balloon is inflated during angioplasty procedures.

The catheter in accordance with the invention generally comprises a flexible, elongated tubular member, a perfusion body, and a balloon member disposed about and sealingly secured to the perfusion body. The flexible tubular member has an inner lumen extending along the length thereof and is adapted to receive a guidewire therein. The perfusion body, which is secured to the distal extremity of the tubular member, has two inner lumens, a first lumen in fluid communication with the inner lumen of the tubular member and a second lumen having a much larger diameter than the first lumen and having inlet and discharge ports to facilitate the passage of blood therethrough when the balloon element disposed about the perfusion body is inflated. The first lumen is preferably adapted to receive a guidewire from the inner lumen of the tubular member.

In a presently preferred embodiment, the balloon member encases the perfusion body and has at least one inlet port in fluid communication with the inlet port of the second lumen of the perfusion body and at least one discharge port in fluid communication with the discharge port of the second lumen of the perfusion body. The perfusion body has an inflation /deflation port in the upper portion thereof in fluid communication with the first lumen therein which opens into the interior of the balloon member to provide inflation fluid thereto. The balloon is sealingly secured about the periphery of the perfusion body distally and proximally of the inflation/deflation port to prevent loss of fluid.

A guiding element or guidewire is disposed within the inner small diameter lumen of the catheter so that the catheter can be more easily steered to the desired location within the patient's coronary vasculature. The core of the guidewire is disposed within the inner lumen of the tubular member, passes through the small diameter first lumen of the perfusion body and extends out the distal end thereof. A helical coil or other flexible body is disposed about and secured to the portion of the guidewire core extending out of the perfusion body. The core wire of the guidewire extends proximally through the inner lumen of the tubular member and the proximal end thereof is secured to a torquing means, such as a knob, to rotate the guidewire when it is advanced through the patient's vasculature to thereby steer the catheter to the desired location. The distal end of the perfusion body is sealingly secured about the core of the guiding element to prevent loss of inflation fluid.

The operation of the steerable catheter of the invention is similar to that of conventional steerable dilatation catheters, except that when the dilatation balloon is inflated, blood is forced to flow distally through the larger second lumen of the perfusion body to the distal end of the catheter and thereby prevent ischemic conditions in tissue distal to the dilatation balloon. These and other advantages of the invention will become more apparent from the following detailed description thereof when taken in conjunction with the accompanying exemplary drawings.

BRIEF DESCRIPTION OF THE DRAWING

FIG. 1 is a longitudinal sectional view of a dilatation catheter embodying features of the invention;

FIG. 2 is a transverse sectional view of the catheter shown in FIG. 1 taken along the lines of 2—2;

FIG. 3 is a transverse sectional view of the catheter shown in FIG. 1 taken along the lines 3—3;

FIG. 4 is a transverse sectional view of the catheter shown in FIG. 1 taken along the lines 4—4; and FIG. 5 is a transverse sectional view of the catheter shown in FIG. 1 taken along the lines 5—5.

DETAILED DESCRIPTION OF THE INVENTION

FIG. 1 illustrates a perfusion dilatation catheter 10 embodying features of the invention which generally comprises an elongated, flexible tubular member 11, a perfusion body 12, and a balloon member 13 disposed about the perfusion body and sealingly secured about the periphery thereof at locations 14 and 15 to prevent loss of liquid during the balloon inflation.

The tubular member 11 has an inner lumen 16 extending along the length thereof which is in fluid communication with the interior of balloon member 13 to direct inflation fluid thereto and which is also adapted to receive a guidewire 17. The proximal end of tubular member 11 is secured to an adapter 18 and the distal end is secured to the proximal end of the perfusion body 12.

The perfusion body 12 has two interior lumens, a first relatively small diameter lumen 20 which is in fluid communication with inner lumen 16 of tubular member 11 and which receives guidewire 17 and a second relatively large diameter lumen 21 having an entry port 22 at the proximal end and a discharge port 23 at the distal end for the passage of blood therethrough. Preferably, the ratio of the large diameter lumen 21 to small diameter lumen 20 is greater than 3:1. The interior of the inner lumen 20 may be enlarged within the interior of the balloon member 13 as shown in FIG. 4.

An inflation/deflation port 24 is provided in the upper surface of perfusion body 12 in fluid communication with the first small diameter lumen 20 to direct inflation fluid to and from the interior of balloon member 13. The distal end of the perfusion body 12 is sealingly secured about the core member 25 of the guidewire 17 but with sufficient clearance to allow the guidewire to rotate.

The balloon member 13 is disposed about the perfusion body 12 and is sealingly secured by adhesive, heat shrinking or other suitable means about the periphery thereof at locations 14 and 15. The proximal end of balloon member 13 is sealingly secured to either the distal end of tubular member 11 or the proximal end of perfusion body 12 or both. The distal end of the balloon 13 is disposed about coil 27 on the distal extremity of the guidewire 17 with sufficient clearance to allow rotation of the guidewire therein.

The lower portions of the balloon member 13 extending proximal to sealing location 14 and distal to sealing location 15 are provided with entry and discharge ports 30 and 31, respectively, which are in fluid communication with the entry and discharge ports 22 and 23 of large lumen 21 in the perfusion body.

Means (not shown) may be provided to allow for the passage of air from the interior of the balloon during the inflation with liquid but which blocks the passage of inflation liquid therefrom, as described in U.S. Pat. Nos. 4,582,181 (Samson), 4,692,200 (Powell) and copending applications Ser. No. 000,651 filed Jan. 6, 1987, and Ser. No. 000,648 all of which have been assigned to the present assignee, and which are incorporated herein by reference thereto.

The adapter 18 on the proximal extremity of the catheter 10 has a first arm 32 which is in fluid communication with the lumen 16 of the tubular member 11 to supply inflation fluid therethrough to the interior of the balloon member 13. The proximal extremity of the core member 25 of guidewire 17 extends through the second arm 33 of adapter 18 and has a torquing knob 34 secured thereto for rotating the guidewire 17 to thereby facilitate steering the distal end of the catheter 10 during the advancement thereof through a patient's vasculature. Details of suitable torquing knobs are found in U.S. Pat. Nos. 4,619,263, 4,641,654 and 4,664,113 previously mentioned. A flexible helical coil 27 preferably formed of radiopaque materials is disposed about the portion of the guidewire 17 extending through the distal end of balloon member 13 and is secured thereto by suitable means, such as soldering or brazing or welding. In the presently preferred embodiment, the distal portion of the core element 25 of the guidewire 17 is tapered and the distal tip thereof is secured to plug 35 which is usually formed of suitable radiopaque material. However, if a more flexible distal tip is desired, the guidewire 17 can be provided with a floppy design (not shown) wherein the core 25 terminates proximal of the plug 35 and a shaping ribbon extends from the distal end of the core to the plug as illustrated in U.S. Pat. Nos. 4,554,929 and 4,538,622.

The catheter of the invention can be advanced through a patient's vascular system to a desired location therein in a conventional fashion as with prior steerable catheters. Knob 34 on the proximal end of adapter 18 is rotated to rotate the flexible coil 27 on the distal tip of the guidewire 17 and thereby direct the tip into the desired arterial branches. Once in position across a lesion, the balloon 13 is inflated with radiopaque liquid which passes through arm 32, inner lumen 16, first lumen 20, and inflation/deflation port 24 to the interior of balloon 13. In dilating a stenosis, the inflated balloon 13 occludes the artery, but blood proximal to the balloon passes through entry ports 30 in the balloon member and entry port 22 of the perfusion body 12, through the large diameter second lumen 21 therein and then is discharged through port 23 and ports 31 in the balloon 13. In this manner, the balloon 13 can be inflated within an artery for long periods of time with little risk in creating ischemic conditions in tissue distal to the balloon 13. Dilatation of arterial stenosis with the catheter of the invention for periods of up to 30 minutes or more are believed to provide long-term protection against re-stenosis and little risk that a dilated artery will collapse when the balloon is deflated. In the event that a dilated stenosis closes down when the balloon 13 is deflated, the catheter of the invention can be reinflated across the lesion and thereby in effect act as a temporary stent to maintain blood flow across the lesion until by-pass surgery or other corrective action can be taken on the blockage.

The tubular member 11 can be formed of suitable thermoplastic material such as polyethylene, polyvinylchloride and the like or from stainless steel (i.e. hypotubing) or it can be of composite structure such as described, in copending application Ser. No. 241,047 filed 9-6-88. In this latter application, the composite structure comprises a tubular substructure formed from material such as polyimide with an outer coating of resin impregnated fibrous material which has been wound or braided into the tubular substructure to provide a relatively stiff proximal portion and a relatively flexible but diametrically rigid distal portion. The balloon may be irradiated polyethylene, polyethylene terephthalate, or other suitable flexible but relatively inelastic materials. The perfusion body 12 can be made from flexible thermoplastic or thermoset plastics, such as polyethylene, polyvinylchloride, polyurethane, and the like.

Typical dimensions of the catheter include an overall length of about 135 to about 175 cm, a tubular member outer diameter of about 0.035 to about 0.45 inch (0.635-1.14 mm) and an inner diameter of about 0.1 to about 0.3 inch (0.254-0.762 mm). The perfusion body has an overall length of about 1.5 to 3.5 inches (3.8-8.9 cm) and an outer diameter at its thickest section of about 0.04 to about 0.075 inch (1.02-1.91 mm). The diameter of the proximal portion of the small inner lumen 20 of the perfusion body 12 is approximately the same as the inner diameter 16 of the tubular member 11 and is greater or smaller depending on whether the proximal end of the perfusion body is secured outside or inside the distal end of the tubular member. However, the diameter thereof may be reduced in the distal direction. The diameter of the large lumen 21 in the perfusion body is sufficiently large to handle the amount of expected blood flow and is usually much larger, i.e., at least 1.5 times the diameter of the first lumen 20. The balloon member 13 generally is of approximately the same length or slightly larger than the perfusion body 12. The entry and discharge ports 30 and 31 in the balloon member 13 are sized to provide adequate blood flow at the blood pressures normally found, e.g., 70 cc/min at 80 mm Hg. The size and number of these apertures can be varied to provide the flow desired. The diameter of the proximal portion of guidewire 17 can range from 0.008 to about 0.018 inch (0.203-0.457 mm) with the distal end of the core member thereof tapering toward the distal end in a conventional manner. The outer diameter of coil 27 is generally smaller than the inner diameter of the tubular member 11 and the inner lumen 20 over essentially all of the length thereof except at the distal extremity which is necked down about the core 25 to prevent the loss of inflation fluid.

While the perfusion catheter of the invention has been described in terms of certain presently preferred embodiments, it should be apparent that modifications may be made. For example, the balloon member and the perfusion body are described herein as separate members which are secured together with the tubular member to form the catheter assembly. However, either of these members may be formed in a unitary structure with the tubular member if desired. Other modifications and improvements can be made without departing from the scope of the invention.

What is claimed is:

1. A steerable perfusion dilatation catheter comprising:
    (a) an elongated tubular member having an inner lumen extending along the interior thereof;
    (b) a tubular perfusion body secured by the proximal end thereof to the distal extremity of the elongated tubular member, said perfusion body having a first, relatively small diameter lumen extending longitudinally therethrough in fluid communication with the inner lumen of the tubular member and having an inflation/deflation port open to the exterior of the perfusion body and a second, relatively large diameter lumen extending longitudinally therethrough with at least one inlet port on the proximal end thereof and at least one discharge port on the distal portion thereof adapted to facilitate the passage of blood therethrough;
    (c) an inflatable dilatation balloon member which is sealably secured by proximal and distal extremities thereof about the perfusion body with the inflation/deflation port of the perfusion body within the interior of the balloon member connecting in fluid communication the first, relatively small diameter lumen within the perfusion body with the interior of the balloon member to facilitate the inflation and deflation thereof; and
    (d) a guiding member extending through and fixed within the small diameter lumen of the perfusion body and having a distal portion extending out the distal end of the balloon, whereby the catheter can be advanced through a patient's vascular system and a stenosis therein, the balloon thereof inflated to dilate the stenosis and blood is perfused through the balloon distal to the catheter.

2. The perfusion dilatation catheter of claim 1 wherein the balloon member extends proximally and distally from the sealing locations thereof about the perfusion body and is provided with at least one inlet port in the proximal extension and at least one discharge port in the distal extension which are, respectively, in fluid communication with the inlet and discharge ports of the relatively large diameter lumen extending through the perfusion body.

3. The perfusion dilatation catheter of claim 1 wherein a guidewire extends through the inner lumen of the tubular member and the first relatively small diameter lumen in the perfusion body and out of the distal end of the balloon member.

4. The perfusion dilatation catheter of claim 1 wherein means are provided to vent air from the interior of the balloon member through the sealed distal end thereof.

5. The perfusion dilatation catheter of claim 1 wherein the diameter of second, relatively large times larger than the diameter of the first, relatively small diameter lumen therein.

6. The perfusion dilatation catheter of claim 1 wherein the tubular member is formed from polyethylene.

7. The perfusion dilatation catheter of claim 1 wherein the tubular member is formed of stainless steel hypotubing.

8. The perfusion dilatation catheter of claim 1 wherein the balloon member is formed from a plastic material selected from the group consisting of polyethylene and polyethyleneterephthalate.

9. The perfusion dilatation catheter of claim 3 wherein the guidewire is provided with torquing means at the proximal end thereof to rotate the guidewire while the catheter is being advanced through the patient's vascular system.

10. The perfusion dilatation catheter of claim 9 wherein the guidewire is fixed within the catheter so as to preclude its removal.

* * * * *